United States Patent [19]
Baldwin et al.

[11] 3,986,645
[45] Oct. 19, 1976

[54] LIQUID DISPENSER

[75] Inventors: Brian E. Baldwin, Wilmette, Ill.;
Alfred C. Einstein, Milwaukee, Wis.;
Ronald D. Baxa, Northbrook, Ill.

[73] Assignee: MPL, Inc., Chicago, Ill.

[22] Filed: May 28, 1975

[21] Appl. No.: 581,663

Related U.S. Application Data

[63] Continuation of Ser. No. 311,374, Dec. 1, 1972, abandoned.

[52] U.S. Cl. ............................ 222/386; 128/218 P
[51] Int. Cl.$^2$ ......................................... A61M 5/315
[58] Field of Search ............... 222/386; 128/218 M, 128/218 P, 218 NV

[56] References Cited
UNITED STATES PATENTS

| | | | |
|---|---|---|---|
| 2,735,430 | 2/1956 | Huber | 128/218 NV |
| 3,151,787 | 10/1964 | Miller | 222/563 X |

FOREIGN PATENTS OR APPLICATIONS

| | | | |
|---|---|---|---|
| 485,801 | 10/1953 | Italy | 128/218 NV |

Primary Examiner—Robert B. Reeves
Assistant Examiner—John P. Shannon
Attorney, Agent, or Firm—Kinzer, Plyer, Dorn & McEachran

[57] ABSTRACT

A liquid dispenser in the form of a syringe having a barrel, with a piston valve/seal slidable in the barrel bore and having a preformed liquid passage hole extending through a slidable elastic main body thereof in which an elastic hour-glass shaped plug seal is removably disposed. A rearwardly extending post fixed on the forward end wall of the barrel bore effects rearward knockout removal of the plug seal from the preformed hole as a function of forward sliding movement of the piston valve/seal in the bore, and a liquid flow passage is formed in the post to enable passage of liquid therepast. The piston valve/seal main body has a plug-containment chamber which is larger than the plug and enables by-pass liquid flow past the plug after dislodgment of the plug into this chamber.

34 Claims, 9 Drawing Figures

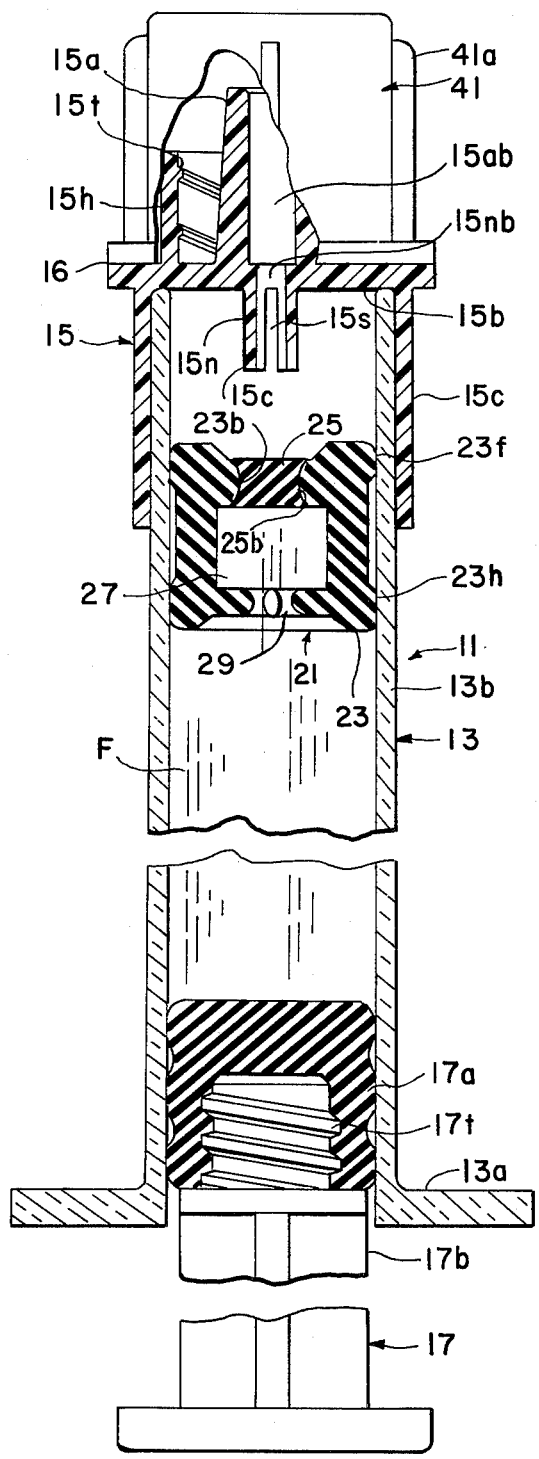
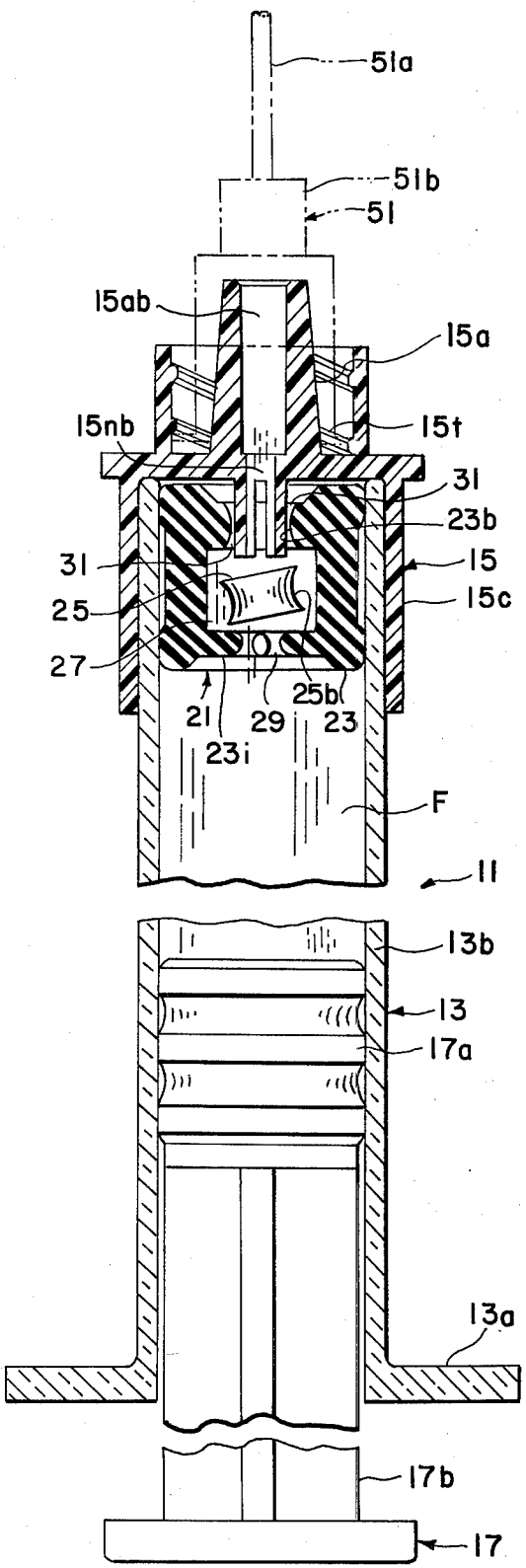
FIG. 1
FIG. 2

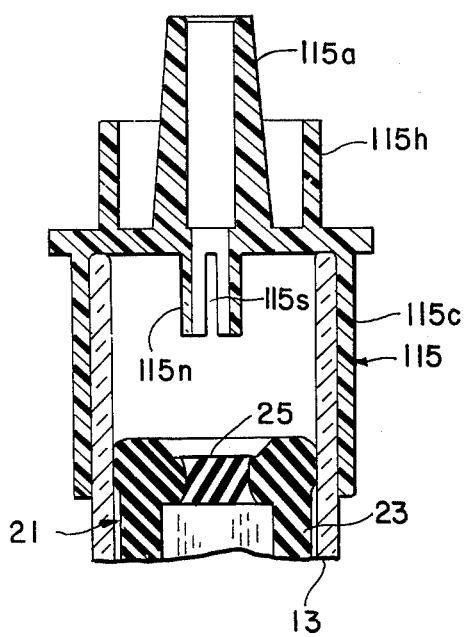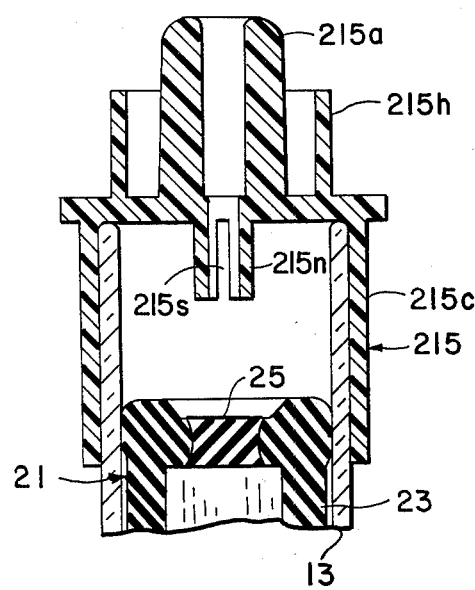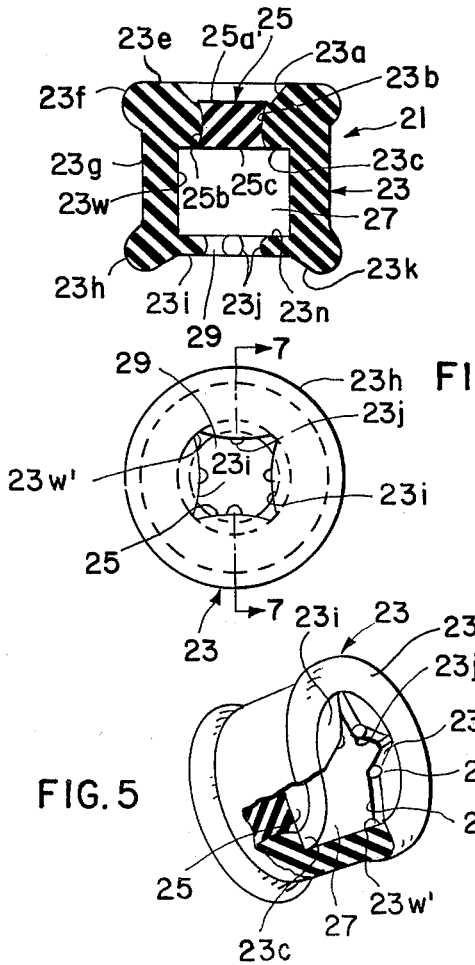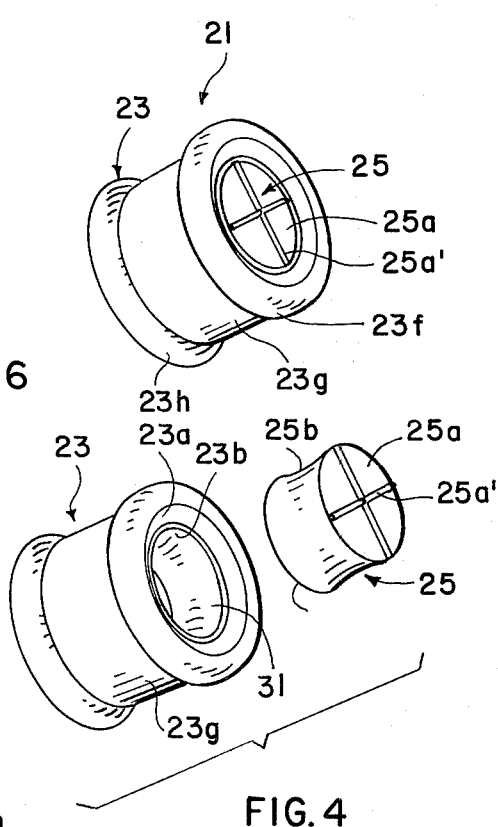

LIQUID DISPENSER

This is a continuation of application Ser. No. 311,374 filed Dec. 1, 1972, now abandoned.

This invention relates to liquid dispensers, and more particularly to manually operable prefilled and sealed syringes or the like from which liquids are discharged.

It is desirable to provide a syringe which incorporates a forward seal which will be automatically opened for liquid flow therethrough as a part of the normal syringe use operation in which the user routinely depresses the manual plunger of the syringe with the exit port pointed upward to remove air from the syringe prior to use, or otherwise moves the manual plunger forward to discharge fluid from the syringe or other dispenser.

It is a feature of the present invention to provide a liquid dispenser in the form of a syringe which incorporates a forward piston valve/seal arrangement which is simple and inexpensive to manufacture and which affords easy and automatic rearward dislodgment of a special hour-glass shaped elastic plug seal, from a preformed plug-seal-retention and liquid-passageway hole in the piston valve main body as a function of forward pressure on the syringe handle and concomitant forward motion of the piston valve/seal. Dislodgment of the plug seal from its seated sealing position is readily accomplished by engaging the plug seal with a rearwardly extending post which is aligned for engagement with the plug seal, and which has a fluid passageway formed therein for flow of liquid therethrough after dislodgment of the plug seal. Subsequent resealing may be obviated by forming a suitable channeled surface or surfaces on one or more of the piston valve/seal main body, the knockout post and/or the dislodgable knockout plug seal. The dislodged plug seal is preferably retained after dislodgment within a by-pass-liquid-passage chamber formed rearward of the preformed hole in which the plug seal is originally elastically seated.

Still further objects and attendant advantages will become apparent to one skilled in the art from a reading of the following detailed description of a physical embodiment constructed in accordance with the invention, taken in conjunction with the accompanying drawings, wherein:

FIG. 1 is a longitudinal section view of a syringe embodiment constructed in accordance with the invention, showing the syringe in a prefilled and sealed condition prior to use.

FIG. 2 is a longitudinal section view showing the syringe of FIG. 1 after forward motion of the piston valve and dislodgment of the plug seal from the piston valve/seal main piston body.

FIG. 3 is a view in perspective showing the forward end of the slidable piston valve/seal of the embodiment of FIGS. 1 and 2.

FIG. 4 is an exploded view of the piston valve/seal.

FIG. 5 is a view in perspective partially cut away, showing the piston valve/seal as viewed generally toward the opposite or rear end and from one side.

FIG. 6 is a rear end view of the piston valve/seal.

FIG. 7 is a longitudinal section view of the piston valve/seal taken on line 7—7 of FIG. 6.

FIG. 8 is a fragmentary longitudinal section view of the front end of a modified syringe according to the invention.

FIG. 9 is a fragmentary longitudinal secton view of a further modified syringe according to the invention.

Referring now in detail to the Figures of the drawings, a liquid dispenser in the form of a syringe 11 is provided, having a barrel 13 with a dispensing nose end section 15, a manually manipulable plunger 17, and a slidable piston valve/seal 21 at or adjacent the forward end of the barrel, 13.

The barrel 13 is formed of a cylindrical tubular main body section 13b having a finger grip 13a formed or secured on its rear end, and having a longitudinal fluid containment bore 13bb extending therethrough and in which is slidably inserted the piston valve/seal 21 and a plunger piston seal 17a, of rubber or other suitable elastic or other sealing material, forming the forward end of plunger 17. The space within the bore 13bb of barrel 13 and lying between the plunger piston seal 17a and forward piston valve/seal 21 forms a compartment for containing a prefilled liquid F, such as a drug or other medicament, or other desired liquid to be dispensed. This liquid may be prefilled in any suitable fashion, as by injecting such through or past the annular periphery of the piston seal 17a, and either after or before complete assembly of the two slidable piston seals 17a and 21 within the bore 13bb.

It will thus be appreciated that by forming the syringe barrel 13, or at least the tubular main body section 13b, of glass or other relatively nonreactive material, and by forming the piston valve/seal 21 and plunger piston seal 17a of rubber or other relatively nonreactive elastomeric or other suitable materials, a liquid may be prefilled and stored within the syringe 11 for a substantial length of time prior to intended ultimate use. It will also be appreciated that if such long-term storage is not desired or necessary, other more reactive materials may be employed, such as plastic, for these liquid storage contact parts.

The barrel 13 may have a nose section 15 formed either integrally therewith or as a separate part secured thereon, as in the illustrative and preferred embodiment. In this illustrative embodiment the nose section 15 includes a tubular sheath portion 15c which may be suitably secured about the forward end of the cylindrical tubular main body section 13b. This nose section 15 may be and is preferably formed of a suitable plastic material, such as polypropylene, nylon, etc., polypropylene being a preferred plastic. The nose section is provided with a nozzle, nipple, or connector tip 15a, which may suitably have a Luer tapered exterior surface for connection with a corresponding Luer connection hub 51b of a needle assembly 51 having a canula 51a thereon. In addition, the nose section 15 is preferably provided with an annular lip extension or flange 15h about which may be initially removably secured a cover 41 which may have gripping and rigidifying ribs 41a extending therealong. Cover 41 may be suitably removably secured to the nose section as by a light heat-sealed staking across the flange interface 16 between cover 41 and nose section 15 to provide a visible tamper-proof seal connection. Annular lip extension 15h may have connector threads 15t formed therewithin, as for instance for use in effecting the securing of a Luer-lock hub 51b onto connector tip 15a.

Connector tip 15a has formed therethrough a fluid discharge bore or orifice 15ab, connecting coaxially with a fluid discharge bore 15nb extending through a dual purpose plug-dislodgment and fluid-passage post 15n formed on and protruding rearwardly from the forward wall 15b of nose section 15. One or more fluid passage by-pass slots or holes 15s is formed in the annular wall of post 15n.

Piston valve/seal 21 may be initially spaced rearwardly from the post 15n, as illustrated, or may be in contact therewith in the pre-use condition if so desired. It is preferred that the piston valve/seal 21 be spaced rearwardly from the post 15n in order to obviate any inadvertent dislodgment of the plug seal 25 from its seat 23b in piston valve/seal 21 prior to dispensing usage of the syringe 11.

In the pre-use condition, the handle 17b of plunger 17 may be disconnected from the rear piston seal 17a, and may be connected in any suitable fashion, as by a threaded connection 17 at the time of desired usage of the syringe.

Piston valve/seal 21, which is preferably formed of rubber as noted heretofore, includes a slidable main piston body 23 within which is removably seated a generally hour-glass or longitudinally concavely shaped plug seal 25. Plug seal 25 is also preferably formed of rubber or other elastomeric material, although such may in a substantially less preferred form be formed of more rigid material. Plug seal 25 is seated and removably self-locked within a generally correspondingly shaped annular plug seal seat 23b. The complementary shaping of the seat 23b and the hour-glass annular surface 25b of plug seal 25 serve to removably self-lock the plug seal 25 in its seated position, and the elastic rubber composition of the seat 23b and plug seal 25 enable relative ease of dislodgment removal of the plug seal 25 from its seated position as a function of forward motion of the piston valve/seal 21 toward and about the post 15n, at which time the plug seal 25 engages with the rearward end 15nc of post 15n and is prevented from further forward movement, while the piston valve/seal main body 23 continues to slide forward toward the forward end face 15b of barrel 13.

The plug seal 25 will thereby be popped out of its seated position within seat 23b, and will move into a plug retention and liquid by-pass chamber or cavity 27 which is formed in fluid connection with the rear face of the initially seated plug seal 25 and the bore 31 formed by seat 23b after dislodgment of plug seal 25 from its seat 23b. The plug retention and liquid by-pass chamber or cavity 27 is bounded by a cylindrical wall 23w which is substantially larger in diameter than the largest diameter of plug seal 25 in its free relaxed condition, and by a forward wall 23c and a rearward wall 23n. The longitudinal distance between chamber forward wall 23c and rear wall 23n is also substantially greater than the longitudinal length of plug seal 25, and it will thus be appreciated that the plug seal 25 is smaller in its free relaxed state in all dimensions than the corresponding interior dimensions of the by-pass and plug retention chamber or cavity 27, thereby enabling by-pass passage of liquid past plug 25 and through bore 31 after the pop-out or knockout dislodgment of plug seal 25 from its seat 23b.

The plug seal 25 is retained against rearward movement out of the cavity or chamber 27 by the rear interior wall 27, this wall being formed by a plurality of retention lips or lip wall segments 23i whch have formed therebetween, as seen in FIGS. 5 and 6, a continuation or extension 23w' of the cylindrical bounding wall 23w of chamber 27, thereby providing a plurality of by-pass channels which enable the passage of fluid past the plug seal 25 and retention lip wall segments 23i when the plug seal is lodged against the rear interior wall surface 23n of the cavity or chamber 27. The retention lips 23i may have formed thereon additional retention nodules 23j to further aid in retaining the plug seal within the chamber 27.

Plug seal 25 has formed on its forward face a rib and channel surface, as indicated at 25a and 25a'. A cross rib configuration 25a' is illustrated, with recessed or channeled surfaces 25a therebetween. Alternatively, the channel face may have a reverse configuration or other channel or groove arrangement may be formed therein to enable fluid by-pass when the plug seal is disposed against the forward wall 23c after dislodgment into the cavity or chamber 27. Alternatively, or in addition, the forward wall 23c may have one or more grooves or channels formed therein to enable this fluid by-pass between the forward wall 23c and plug seal 25 after dislodgment of the plug seal from its seated and sealed position within seat 23b, and if so desired the opposite or rear end of plug seal 25 may also be suitably channelled in lieu of or in addition to the channels formed at 23w' between lip segments 23i.

In the free relaxed condition of piston valve/seal 21, it is preferred that the plug seal 25 form a substantially fully complementary sized seated seal with its seat 23b along the seat/seal interface therebetween. Radial compressive interaction between plug seal 25 and the seat 23b will be effected through the radial sealing compression of piston main body 23 when such is inserted in sliding relation within the barrel bore 13bb, which bore is preferably of smaller diameter than the free relaxed outer diameter of sealing rings 23f and 23h formed at the opposite ends of the slidable piston valve/seal 21. Thus, the compressive sealing interaction of the rigid glass wall 13b of barrel 13 on the elastic piston main body sealing rings 23f, 23h, will effect a radial compressive action on the piston main body 23 and at the seal/seat interface 25b, 23b, thereby providing increased sealing action at this interface. As noted heretofore, however, the elastic interface will enable the ready dislodgment of the plug seal 25 from seat 23b by forward motion of the slidable piston valve/seal 21 and engagement thereof with the rearwardly extending post 15n.

During this initial movement of the piston valve/seal 21 forwardly and prior to dislodgment of the plug seal 25 from its seated position within seat 23b, the air in the forward pocket around post 15n and forward of piston valve/seal 21 will be ejected through slot 15s and bore 15nb, 15ab in post 15n and connector tip 15a. Slot, or slots, 15s in post 15n enables ease of continued discharge of this air through the bore 15nb, 15a, after engagement of the post 15n with plug seal 25 and prior to dislodgment of the plug seal from its seat 23b, although sufficiently deep face channels 25a on plug 25 or on post end 15nc may also perform this function, assuming a loose fluid passage fit between seat 23b and the outer wall of post 15n. It is preferred that the post 15n have a diameter which is less than the smallest diameter of bore 31 formed by seat 23b, so as to provide relatively less resistance to continued forward travel of the piston main body 23 along and about the post 15n during and after dislodgment of the plug seal 25. By use of the side slot or slots 15s, this larger diameter relationship is not a critical necessity as the side slot 15s will enable complete fluid connection between all sections of the bore 13bb both forwardly and rearwardly of the piston valve/seal 21, after dislodgment of the plug seal 25 from its seat 23b.

Exterior end walls 23a and 23k of piston valve main body 23 are preferably inwardly tapered in order to aid in movement of air bubbles toward the center of the piston valve/seal for discharge through the exit bore 15nb, 15ab at the time of preparing the syringe for injection or other use.

In operation, the operator will first remove the cover 41 from the nose section 15, and will thereupon secure a needle 51 to the connector tip 15a, assuming that a needle 51 is to be employed in the dispensing operation. Handle 17b is then connected to the piston seal 17a. The operator may then hold the syringe 11 in an upright position with its nose section 15 extending upwardly, and thereupon press upwardly on plunger 17 to thereby move piston seal 17a forward toward the nose end. The forward motion of piston seal 17a will effect a hydraulic ram force action on piston valve/seal 21 through the liquid F and any air contained between plunger piston seal 17a and piston valve/seal 21, thereby causing forward movement of the piston valve/seal 21. The forward movement of piston valve/seal 21 will effect a pop-out dislodgment or knockout of plug seal 25 from its seat 23b through the resistive interengagement between post 15n and plug seal 25 during the continued forward movement of the slidable main body 23 by the hydraulic ram force action thereon from plunger 17 and fluid F. The dislodged plug seal 25 will be contained within the liquid by-pass and retention chamber 27, and further forward movement of the plunger 17 will enable the operator to eject the air from the liquid containment chamber, and thereafter to eject the liquid through the needle 51 and into a patient, or to otherwise discharge the liquid through the bore 15nb, 15ab, as may be desired for a particular use.

FIGS. 8 and 9 illustrate alternative syringe nose end embodiments, the embodiment of FIG. 8 being provided with a nose section 115 having a cover sleeve or sheath 115c corresponding to sleeve 15c of FIG. 1, and a lip extension 115h corresponding to annular lip extension 15h of FIG. 1. A connector tip 115a may be suitably shaped for a conventional Luer tapered hub connection, without the employment of threads 15h as in FIG. 1. A plug-knockout post 115n with slot 115s therein corresponds to post 15n and slot 15s of FIG. 1.

In the modification of FIG. 9, similar corresponding parts are provided, with the nose being indicated by corresponding 200 series numbers, an oral nipple or nozzle 215a being provided in lieu of connector tip 15a, 115a of FIGS. 1 and 8.

While the invention has been illustrated and described with respect to several illustrative embodiments, it will be apparent that various modifications and improvements may be made without departing from the scope and spirit of the invention. For instance, the plug containment and liquid by-pass chamber arrangement may be used with other piston plug seal configurations, if loss of the attendant advantages of the preferred plug seal configuration can be tolerated in a given instance, or the hour-glass plug seal may be utilized without the plug seal containment and liquid by-pass chamber, if in a particular use the containment of the plug seal, after dislodgment or knockout from its seat/seal, is not necessary or desired. The combined arrangement is, however, must preferred. Also, while the particular smoothly longitudinally concave annular configuration for the generally hour-glass surface 25b is particularly advantageous and much preferred, other generally hour-glass shaped or longitudinally concave surfaces 25b may be employed. Accordingly, it is to be understood that the invention is not to be limited to the illustrative embodiments, but only by the scope of the appended claims.

We claim:
1. A liquid dispenser comprising
a barrel having a liquid discharge orifice and a liquid containment chamber bore for connection with said discharge orifice,
a piston valve/seal slidably disposed in sealing relation in said bore and having a preformed liquid passage hole extending through a piston valve/seal main piston body thereof in which a knockout plug seal is removably elastically disposed,
said knockout plug seal having an annular generally hour-glass peripheral shape,
a rearwardly extending post disposed in said bore and more resistant to movement than said piston valve/seal, said post being engageable wth said plug as a function of forward sliding movement of said piston valve/seal in said bore, to effect rearward knockout removal of said hour-glass-shaped plug seal from said liquid passage hole,
and a manually manipulable liquid-flow-effecting piston disposed rearwardly of said piston valve/seal,
said piston valve/seal main piston body having a plug-seal-retaining cavity larger than said plug seal to permit fluid flow past said plug seal when said plug seal is ejected into said plug-seal-retaining cavity and connecting with said bore for ejection of plug seal thereinto as a function of interengagement between said post and said plug seal,
said plug-seal-retaining cavity being open at its rear end for fluid flow therethrough.
2. A dispenser according to claim 1,
said piston valve/seal main piston body and said plug seal being formed of elastomeric material.
3. A dispenser according to claim 2, said open rear end of said cavity having an end opening a portion of which is larger in cross-section than the relaxed size of said plug seal and a portion of which opening is smaller than said plug seal to thereby retain said plug seal after ejection into said cavity, while aiding in enabling fluid flow therepast and through said opening.
4. A dispenser according to claim 3,
the interface between said open rear end of said cavity and said plug seal being of interrupted configuration and providing a fluid flow interface channel therepast.
5. A dispenser according to claim 4,
said interface channel being formed between the annular peripheral surface of said plug seal and the adjacent peripheral wall surface forming said hole.
6. A dispenser according to claim 4,
and the interface between the rear wall surface bounding said liquid passage hole and the forwardly facing surface of said plug seal upon ejection of said plug seal into said cavity being of interrupted configuration and forming a fluid flow channel therepast.
7. A dispenser according to claim 1,
the interface between said open rear end of said cavity and said plug seal being of interrupted configuration and providing a fluid flow channel therepast.
8. A dispenser according to claim 7, said interface channel being formed between the annular peripheral surface of said plug seal and the adjacent peripheral wall surface forming said hole.

9. A dispenser according to claim 7, and the interface between the rear wall surface bounding said liquid passage hole and the forwardly facing surface of said plug seal upon ejection of said plug seal into said cavity being of interrupted configuration and forming a fluid flow channel therepast.

10. A dispenser according to claim 1 said bore having a forward end wall on which said post is fixed and from which said post protrudes rearwardly therefrom.

11. A dispenser according to claim 10, said post having a liquid passage channel formed therein and communicable with said discharge orifice.

12. A dispenser according to claim 11, said channel being a bore extending through said post and communicating with said discharge orifice.

13. A dispenser according to claim 12, an anti-blocking laterally extending liquid passage channel formed on said post to effectively prevent forward liquid flow blockage between said plug seal, piston valve/seal main piston body and post after rearward dislodgment of said plug seal from said hole.

14. A dispenser according to claim 1, said plug-seal-retaining cavity being larger in all corresponding dimensions than said plug seal.

15. A liquid dispenser comprising
a barrel having a liquid discharge orifice and a liqid containment chamber bore for connection with said discharge orifice,
a piston valve/seal slidably disposed in sealing relation in said bore and having a preformed liquid passage hole extending through a piston valve/seal main piston body thereof in which a knockout plug seal is removably elastically disposed;
a rearwardly extending post disposed in said bore and more resistant to movement than said piston valve seal, said post being engageable with said plug as a function of forward sliding movement of said piston valve/seal in said bore, to effect rearward knockout removal of said plug seal from said liquid passage hole,
and a manually manipulable liquid-flow-effecting piston disposed rearwardly of said piston valve/-seal,
said piston valve/seal main piston body having a plug-seal-retaining cavity larger than said plug seal to permit fluid flow past said plug seal when said plug seal is ejected into said plug-seal-retaining cavity and connecting with said bore for ejection of said plug seal thereinto as a function of interengagement between said post and said plug seal,
said plug-seal-retaining cavity being open at its rear end for fluid flow therethrough.

16. A dispenser according to claim 15, said post having a liquid passage channel formed therein and communicable with said discharge orifice.

17. A dispenser according to claim 16, said channel being a bore extending through said post and communicating with said discharge orifice.

18. A dispenser according to claim 17, an anti-blocking laterally extending liquid passage channel formed on said post to effectively prevent forward liquid flow blockage between said plug seal, piston valve/seal main piston body and post after rearward dislodgment of said plug seal from said hole.

19. A dispenser according to claim 15, said piston valve/seal main piston body and said plug seal being formed of elastomeric material.

20. A dispenser according to claim 19, said open rear end of said cavity having an end opening a portion of which is larger in cross-section than the relazed size of said plug seal and a portion of which opening is smaller than said plug seal to thereby retain said plug seal after ejection into said cavity, while aiding in enabling fluid flow therepast and through said opening.

21. A dispenser according to claim 19, the interface between said open rear end of said cavity and said plug seal being irregular and providing a fluid flow channel therepast.

22. A dispenser according to claim 21, said interface channel being formed between the annular peripheral surface of said plug seal and the adjacent peripheral wall surface forming said hole.

23. A dispenser according to claim 21, and the interface between the rear wall surface bounding said liquid passage hole and the forwardly facing surface of said plug seal upon ejection of said plug seal into said cavity being of interrupted configuration and forming a fluid flow channel therepast.

24. A dispenser according to claim 15, the interface between said open rear end of said cavity and said plug seal being of interrupted configuration and providing a fluid flow channel therepast.

25. A dispenser according to claim 24, said interface channel being formed between the annular peripheral surface of said plug seal and the adjacent peripheral wall surface forming said hole.

26. A dispenser according to claim 24, and the interface between the rear wall surface bounding said liquid passage hole and the forwardly facing surface of said plug seal upon ejection of said plug seal into said cavity being of interrupted configuration and forming a fluid flow channel therepast.

27. A dispenser according to claim 15, said plug-seal-retaining cavity being larger in all corresponding dimensions than said plug seal.

28. A liquid dispenser comprising
a barrel having a liquid discharge orifice and a liquid containment chamber bore for connection with said discharge orifice,
a piston valve/seal slidably disposed in sealing relation in said bore and having a preformed liquid passage hole extending through a piston valve/seal main piston body thereof in which a knockout plug seal is removably elastically disposed,
means to effect knockout removal of said plug seal from said liquid passage hole,
and a manually manipulable liquid-flow-effecting piston disposed rearwardly of said piston valve/-seal,
said piston valve/seal main piston body having a plug-seal-retaining cavity larger than said plug seal to permit fluid flow past said plug seal when said plug seal is ejected into said plug-seal-retaining cavity and connecting with said bore for ejection of said plug seal thereinto, said plug-seal-retaining cavity being open at its outer end for fluid flow therethrough.

29. A liquid dispenser according to claim 28,
said plug-seal-retaining cavity being disposed rearwardly of said liquid passage hole in which said plug seal is removably elastically disposed.

30. A liquid dispenser according to claim 28,
said piston valve/seal main piston body and plug seal being formed of elastomeric material.

31. A liquid dispenser according to claim 28,
the interface between said open outer end of said cavity and said plug seal being of interrupted configuration and providing a fluid flow interface channel therepast.

32. A liquid dispenser according to claim 31,
and the interface between the wall surface bounding said liquid passage hole and the adjacent interfacing surface of said plug seal upon ejection of said plug seal into said cavity being of interrupted configuration and forming a fluid flow channel therepast.

33. A liquid dispenser according to claim 28,
and the interface between the wall surface bounding said liquid passage hole and the adjacent interfacing surface of said plug seal upon ejection of said plug seal into said cavity being of interrupted configuration and forming a fluid flow channel therepast.

34. A liquid dispenser according to claim 28, said open outer end of said cavity having an end opening, a portion of which is larger in cross-section than the relaxed size of said plug seal and a portion of which opening is smaller than said plug seal to thereby retain said plug seal after injection into said cavity, while aiding in enabling fluid flow therepast and through said outer end opening.

* * * * *